United States Patent
Zhang et al.

(10) Patent No.: US 10,607,342 B2
(45) Date of Patent: Mar. 31, 2020

(54) ATLAS-BASED CONTOURING OF ORGANS AT RISK FOR RADIATION THERAPY

(71) Applicant: Siemens Healthcare GmbH, Erlangen (DE)

(72) Inventors: Li Zhang, Princeton, NJ (US); Shanhui Sun, Princeton, NJ (US); Shaohua Kevin Zhou, Plainsboro, NJ (US); Daguang Xu, Princeton, NJ (US); Zhoubing Xu, Plainsboro, NJ (US); Tommaso Mansi, Plainsboro, NJ (US); Ying Chi, Beijing (CN); Yefeng Zheng, Princeton Junction, NJ (US); Pavlo Dyban, Forchheim (DE); Nora Hünemohr, Stuttgart (DE); Julian Krebs, Moers (DE); David Liu, Richardson, TX (US)

(73) Assignee: Siemenes Healthcare GmbH, Erlangen (DE)

( * ) Notice: Subject to any disclaimer, the term of this patent is extended or adjusted under 35 U.S.C. 154(b) by 218 days.

(21) Appl. No.: 15/625,380

(22) Filed: Jun. 16, 2017

(65) Prior Publication Data
US 2018/0096478 A1    Apr. 5, 2018

Related U.S. Application Data

(60) Provisional application No. 62/401,972, filed on Sep. 30, 2016, provisional application No. 62/401,982, filed on Sep. 30, 2016.

(51) Int. Cl.
G06K 9/00 (2006.01)
G06T 7/00 (2017.01)
(Continued)

(52) U.S. Cl.
CPC .......... *G06T 7/0012* (2013.01); *A61B 5/7246* (2013.01); *A61B 5/7282* (2013.01); *G06N 3/0454* (2013.01); *G06N 3/08* (2013.01); *G06N 7/005* (2013.01); *G06N 20/00* (2019.01); *G06T 3/0075* (2013.01); *G06T 7/12* (2017.01); *G06T 7/149* (2017.01); *G06T 7/60* (2013.01); *G16H 30/20* (2018.01); *G16H 30/40* (2018.01);
(Continued)

(58) Field of Classification Search
None
See application file for complete search history.

(56) References Cited

U.S. PATENT DOCUMENTS 8,848,997 B2 * 9/2014 Fenchel ................. A61B 5/055
382/131
9,305,358 B2 * 4/2016 Matthews ................. G06T 7/11
(Continued)

OTHER PUBLICATIONS

Acosta et al., "Multi-atlas-based segmentation of pelvic structures from CT scans for planning in prostate cancer radiotherapy" (Year: 2013).*
(Continued)

*Primary Examiner* — Soo Jin Park

(57) ABSTRACT

Embodiments can provide a method for atlas-based contouring, comprising constructing a relevant atlas database; selecting one or more optimal atlases from the relevant atlas database; propagating one or more atlases; fusing the one or more atlases; and assessing the quality of one or more propagated contours.

16 Claims, 19 Drawing Sheets

(51) Int. Cl.

| | | |
|---|---|---|
| *G06T 3/00* | (2006.01) | |
| *G06T 7/60* | (2017.01) | |
| *A61B 5/00* | (2006.01) | |
| *G16H 50/30* | (2018.01) | |
| *G06N 20/00* | (2019.01) | |
| *G06T 7/149* | (2017.01) | |
| *G16H 50/50* | (2018.01) | |
| *G16H 70/20* | (2018.01) | |
| *G06T 7/12* | (2017.01) | |
| *G16H 30/20* | (2018.01) | |
| *G16H 50/20* | (2018.01) | |
| *G16H 30/40* | (2018.01) | |
| *G06N 3/04* | (2006.01) | |
| *G06N 3/08* | (2006.01) | |
| *G06N 7/00* | (2006.01) | |

(52) U.S. Cl.
CPC ............ *G16H 50/20* (2018.01); *G16H 50/30* (2018.01); *G16H 50/50* (2018.01); *G16H 70/20* (2018.01); *G06T 2200/24* (2013.01); *G06T 2207/10081* (2013.01); *G06T 2207/10088* (2013.01); *G06T 2207/20076* (2013.01); *G06T 2207/20081* (2013.01); *G06T 2207/20092* (2013.01); *G06T 2207/20101* (2013.01); *G06T 2207/20128* (2013.01)

(56) References Cited

U.S. PATENT DOCUMENTS

| | | | |
|---|---|---|---|
| 9,373,173 B2 * | 6/2016 | Weistrand | ............... G06T 7/149 |
| 9,489,733 B2 * | 11/2016 | Seifert | ................. G06T 7/0012 |
| 9,965,857 B2 * | 5/2018 | Matthews | ............. G06T 7/0016 |
| 10,169,871 B2 * | 1/2019 | Hibbard | .................... G06T 7/38 |

OTHER PUBLICATIONS

Langerak et al., "Label fusion in atlas-based segmentation using a selective and iterative method for performance level estimation (SIMPLE)", IEEE Transactions on Medical Imaging, vol. 29, issue 12, Dec. 2010 (Year: 2010).*

Rikxoort et al., "Adaptive local multi-atlas segmentation: application to heart segmentation in chest CT scans", Medical Imaging 2008 (Year: 2008).*

Wohlhart, et al; "Learning descriptors for object recognition and 3D pose estimation", 2015 IEEE Conference on Computer Vision and Pattern Recognition (CVPR), IEEE, Jun. 7, 2015.

* cited by examiner

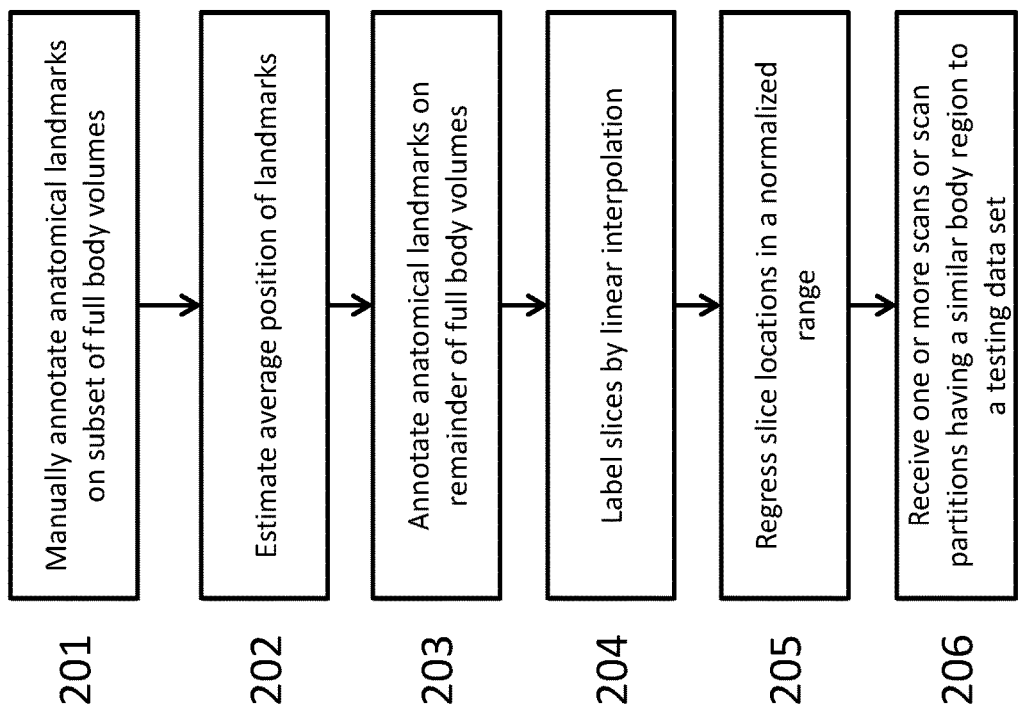

ATLAS-BASED CONTOURING OF ORGANS AT RISK FOR RADIATION THERAPY

CROSS-REFERENCE TO RELATED APPLICATIONS

This application claims the benefit of U.S. Provisional Application Ser. Nos. 62/401,972, filed Sep. 30, 2016, and 62/401,982, filed Sep. 30, 2016, which are incorporated herein by reference in their entirety.

TECHNOLOGY FIELD

The present invention relates generally to methods, systems, and apparatuses for providing contouring of organs at risk for radiation therapy through deep-learning atlas databases.

BACKGROUND

The main purpose of atlas selection is to retrieve scans in the database that are similar to the testing subject, in terms of anatomy and intensity distribution, for optimal contour propagation. In atlas based approaches, atlases are selected for each organ to accommodate inter-subject variability. Traditional atlas fusion aggregates the propagated masks (from contours) by local information without shape priors or models, consequently the final results are likely non-smooth or unrealistic with isolated contours.

SUMMARY

Embodiments can provide a computer-implemented method for atlas-based contouring, comprising constructing a relevant atlas database; selecting one or more optimal atlases from the relevant atlas database; propagating one or more atlases; fusing the one or more atlases; and assessing the quality of one or more propagated contours.

Embodiments can further provide a method further comprising manually annotating one or more anatomical landmarks on a subset of full body volumes; estimating an average position for each of the one or more anatomical landmarks; annotating the one or more anatomical landmarks on a remainder of full body volumes; labelling one or more slices by linear interpolation; regressing one or more slice locations in a normalized range; and retrieving one or more scans having a similar body region to a testing data set.

Embodiments can further provide a method wherein the one or more anatomical landmarks comprise one or more of: a head top, a neck, a lung top, a spine, a knee, and a foot.

Embodiments can further provide a method further comprising defining, by a user, one or more organ templates for one or more testing data sets from a mixed body region database; extending the one or more organ templates as comprehensive representations of required contouring.

Embodiments can further provide a method further comprising extending the one or more organ templates as a comprehensive representation of one or more of: image modality and quality, organ shape and appearance, and annotation protocol.

Embodiments can further provide a method further comprising determining a reference atlas; mapping the one or more atlases in the relevant atlas database to the reference atlas; for each atlas, calculating and storing a mapping $\psi$; for each atlas, calculating and storing a warped atlas and a mask; mapping a testing scan to the reference atlas using a mapping $\psi_{test}$; and selecting atlases with a small mapping difference from $\psi_{test}$ as the one or more optimal atlases.

Embodiments can further provide a method further comprising selecting an atlas from the relevant atlas database; mapping all remaining atlases to the selected atlases using a mapping $\psi_i$; selecting a reference atlas $A_m$; remapping the all remaining atlases to the reference atlas using a mapping $\psi_i^m$; updating the reference atlas by averaging one or more warped atlases with mapping $\psi_i^m(A_i)$; and terminating upon convergence of the reference atlas.

Embodiments can further provide a method further comprising selecting the reference atlas $A_m$ using a medium of a sum of one or more squared values of the mapping $\psi_i$.

Embodiments can further provide a method wherein the mapping $\psi$ is affine or affine+deformable.

Embodiments can further provide a method further comprising formulating a similar atlas search as a K-nearest neighbor search in a mapped manifold M; for each image in the relevant atlas database; mapping the manifold M by calculating a d-dimension feature F; for each image; pairing with a similar image and a dissimilar image to form a triplet; and combining one or more triplet terms with similar pair-wise terms.

Embodiments can further provide a method further comprising using one or more ground truth annotations or organs to form one or more similar and dissimilar pairs; mapping one or more new testing images, without an organ mask input, into the manifold M to a location adjacent to one or more images with similar organ masks; and introducing a spatial transformer layer in a triplet network.

Embodiments can further provide a method further comprising training a triplet network to map one or more images to a separate manifold; using the trained triplet network to map one or more new images to the separate manifold; and adding one or more high quality images to the relevant atlas database.

Embodiments can further provide a method further comprising providing one or more annotation masks and one or more original images in different channels; pairing high quality or low quality annotations separately as similar samples; mixing high quality annotations and low quality annotations to form dissimilar pairs; correlating the one or more annotation masks and one or more original images; and learning a geometric relationship to distinguish the high quality annotations from the low quality annotations.

Embodiments can further provide a method further comprising performing a deep learning based slice normalization; performing a global affine registration to align one or more organs such that the one or more organs fit into a region of interest on a target image; performing a poly-affine registration; and performing a diffeomorphic registration.

Embodiments can further provide a method further comprising registering each of the one or more optimal atlases to a reference atlas Am with a mapping $\psi_i^m$; for each optimal atlas, propagating one or more contours to a reference space; registering the reference atlas to a testing scan using a mapping $\phi_{test}$; and for each atlas, propagating one or more contours $C_i$ of each atlas to the testing scan by $\phi_{test}\psi_i^m(C_i)$.

Embodiments can further provide a method further comprising combining the one or more propagated contours through vote collection; checking an area of a combined mask derived from the one or more propagated contours; and determining the area closest to a reference atlas mask.

Embodiments can further provide a method further comprising assessing a confidence of each of the one or more propagated contours; for each of one or more voxels, calculating a sum of a squared difference of image intensities; and weighing a reliability of each of the one or more propagated contours.

Embodiments can further provide a method further comprising aggregating a mask from each of the one or more propagated contours; generating a probability map; and fitting a pre-trained organ shape model to the probability map.

Embodiments can further provide a method further comprising using an encoder and decoder network to implicitly learn shape models; compressing information from an entire image field to a vector; combining the masks to form the probabilistic map; providing the probabilistic map as a separate channel to train the encoder and decoder network; and training the encoder and decoder network to fit one or more PCA shape models to the probabilistic map.

Embodiments can further provide a method wherein the assessing the quality of one or more propagated contours is performed using at least one of metrics, machine learning, a deep neural network, and metric learning.

In another illustrative embodiment, a computer program product comprising a computer usable or readable medium having a computer readable program is provided. The computer readable program, when executed on a processor, causes the processor to perform various ones of, and combinations of, the operations outlined above with regard to the method illustrative embodiment.

In yet another illustrative embodiment, a system is provided. The system may comprise a processor configured to perform various ones of, and combinations of, the operations outlined above with regard to the method illustrative embodiment Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIGS. 2A-2B illustrate the construction of relevant atlas databases, in accordance with embodiments described herein;

DETAILED DESCRIPTION OF ILLUSTRATIVE EMBODIMENTS

Figure 1:
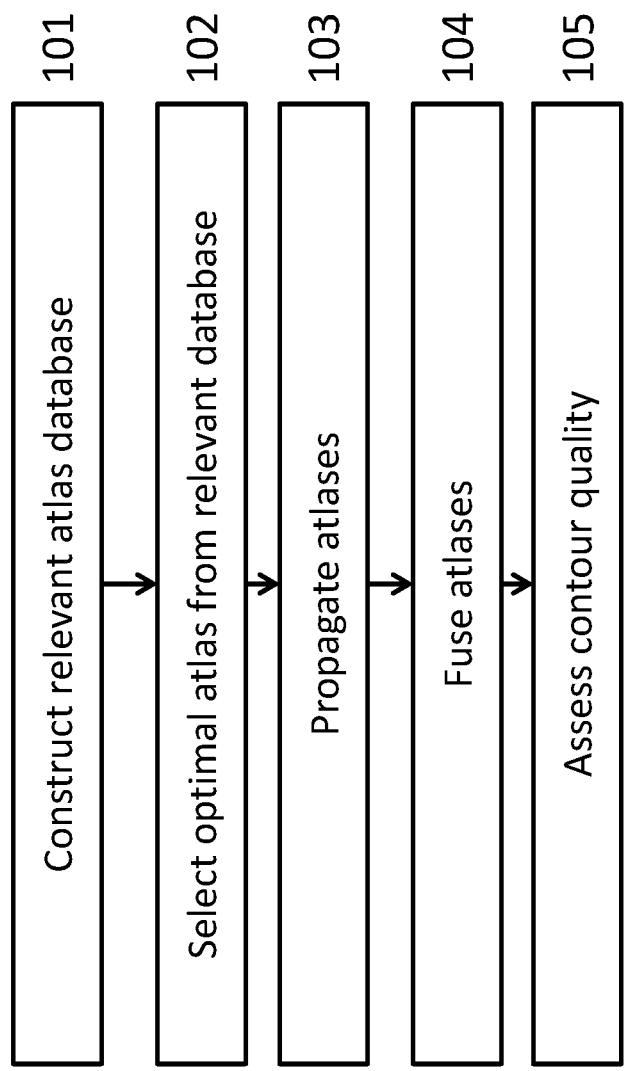
FIG. 1 illustrates a method for atlas-based contouring of organs at risk for radiation therapy, in accordance with embodiments described herein.

In an embodiment, the novel atlas workflow fulfills the clinical need of organ contouring by constructing a relevant atlas database, and then propagates contours from this relevant atlas database for general organ segmentation, without the constraints of specific body regions. The system can also use deep learning techniques for significant improvements on robustness and accuracy of each major component in atlas-based approaches, as well as the overall workflow. Moreover, the system can train the deep-learning components together for an end-to-end deep learning based atlas contouring system. FIG. 1 illustrates a method for atlas-based contouring of organs at risk for radiation therapy. The five main components in the method can be constructing a relevant atlas database 101, selecting an optimal atlas from the relevant database 102, propagating atlases 103, fusing atlases 104, and assessing contour quality 105.

Figure 2B:
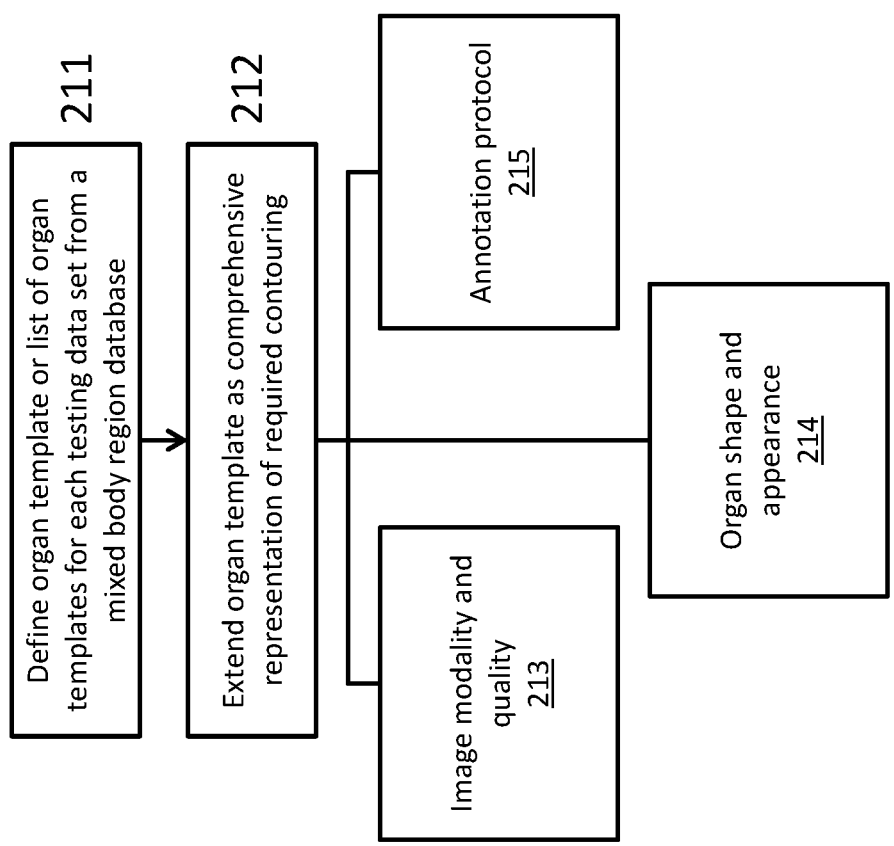

FIGS. 2A and 2B illustrate the construction of relevant atlas databases, in accordance with embodiments described herein. To construct the relevant atlas database, the system can use a deep learning based fine-grained body part recognition approach to select scans or scan partitions that have a similar body region to the testing data set.

In an embodiment, the system can perform an atlas retrieval by a testing scan. First, six anatomical landmarks, e.g. head top, neck, lung top, spine, knee, and foot, can be manually annotated on one or more full body volumes 201 to estimate the average positions of the landmarks 202. The six landmarks can be used to build a normalized body height model. Then, the landmarks in the remaining volumes can be annotated 203 and slices can be labeled by linear interpolation 204. The deep learning based body part recognition can then be trained to regress slice location in a normalized range (e.g., [0 1]) 205 for fine-granularity recognition. The system can then receive one or more scans or scan partitions having a similar body region to a testing data set 206.

In an alternate embodiment, the system can perform an atlas retrieval by organ template. The system uses organ templates to retrieve atlas from a mixed body region database. An organ template or a list of organ templates can be defined by a user for each testing data set 211. For instance, if a liver organ template is provided, the system can retrieve atlases from the database based on the normalized values of liver. This organ template can further be extended as a comprehensive representation of required contouring 212, including but not limited to, the image modality and quality 213, organ shape and appearance 214, and the annotation protocol 215.

Figure 3A:
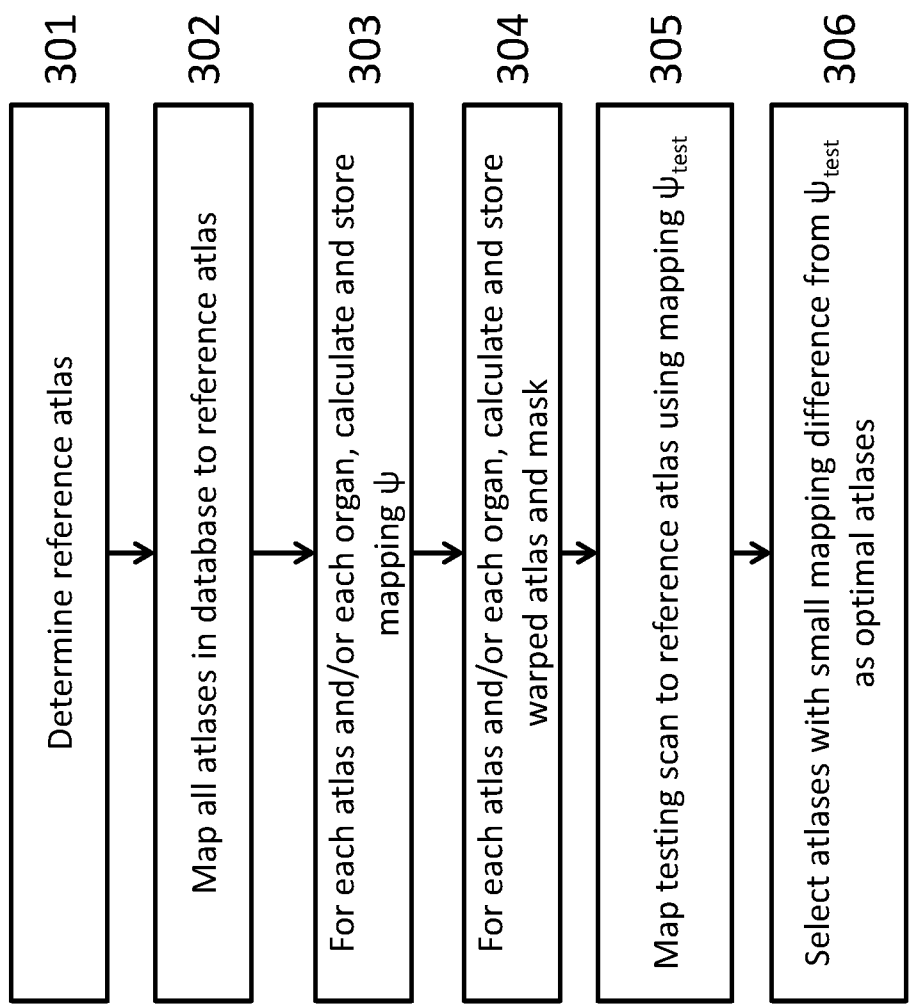
FIG. 3A illustrates the selection of an optimal atlas, in accordance with embodiments described herein.
Figure 4:
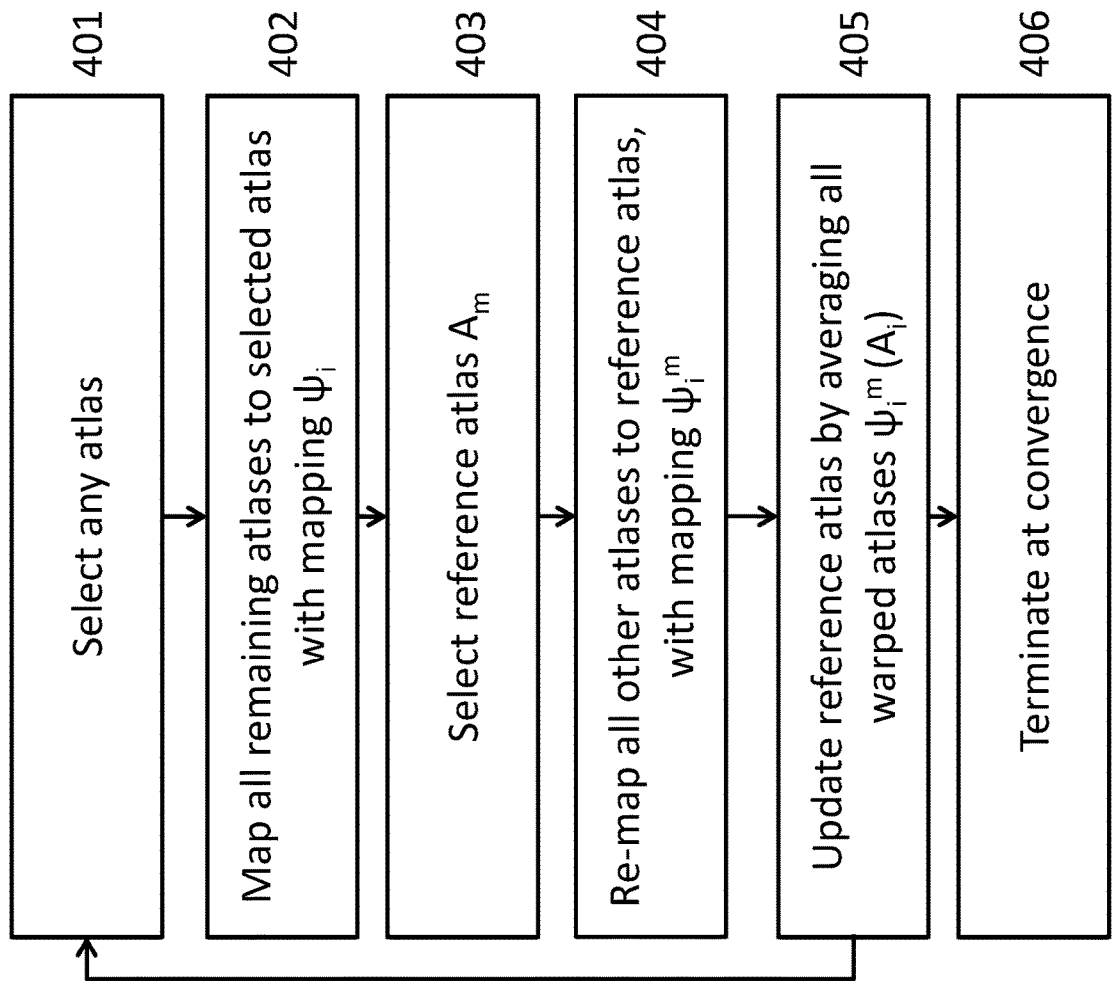
FIG. 4 illustrates the selection of a reference atlas, in accordance with embodiments described herein.

FIG. 3A illustrates the selection of an optimal atlas, in accordance with embodiments described herein. First, the system can determine a reference atlas 301. FIG. 4 illustrates the selection of a reference atlas, in accordance with embodiments described herein. First, the system can select any atlas from the relevant database 401, then can map all the remaining atlases to the selected atlas with mapping $\psi_i$ 402. The system can then, select a reference atlas $A_m$ 403. In an embodiment, the system can select a reference atlas by the medium of sum of the squared values of mapping $\psi_i$. The system can then re-map all the other atlases to reference atlas $A_m$, using a mapping $\psi_i^m$. As an optional step, the system can update the reference atlas by averaging all the warped atlases $\psi_i^m (A_i)$ 405. The system can then repeat the preceding steps several times until convergence is achieved 406.

Returning to FIG. 3A, once the reference atlas is determined 301, the system can map all atlases in the database to the reference atlas 302. The system can then, for each atlas and/or each organ, calculate and store mappings $\psi$ 303. In an embodiment, the mappings can be affine or affine+deformable. The warped atlas and mask can then also be stored for each atlas and/or each organ 304. Then the optimal atlas selection can be scan-based or organ-based. For a new testing scan, the scan can be first mapped to the reference atlas with mapping $\psi_{test}$ 305, and then the atlases with small mapping difference from $\psi_{test}$ can be selected as the optimal atlases 306.

Figure 3B:
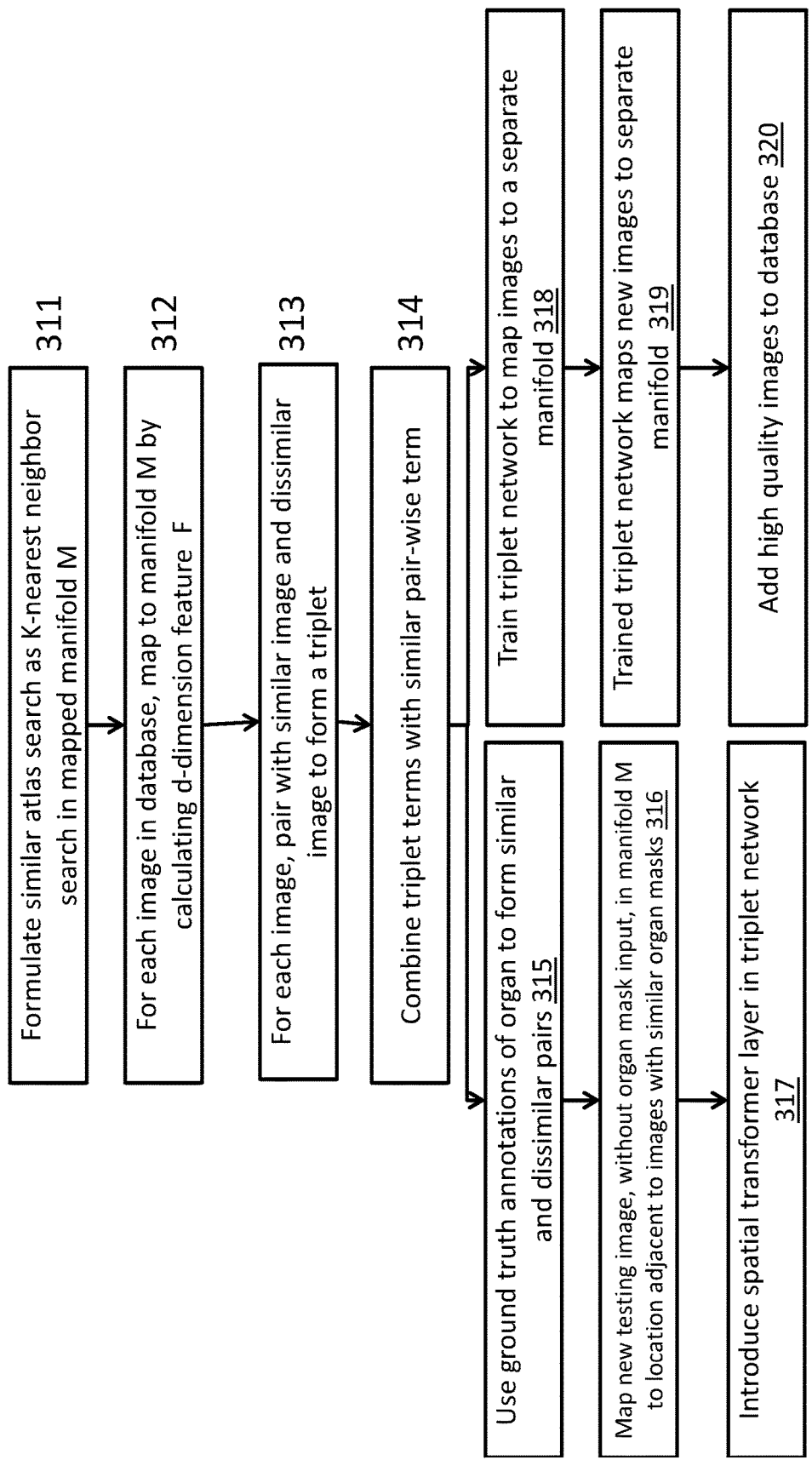
FIG. 3B illustrates the use of similarity learning for atlas selection, in accordance with embodiments described herein.

FIG. 3B illustrates the use of similarity learning for atlas selection, in accordance with embodiments described herein. In light of the metric learning concept in document retrieval field, the system can retrieve similar images or atlases from the database using metric learning. In an embodiment, the metric learning can be a triplet network. That is, the system can formulate the similar atlas search as a K-nearest neighbor search in a mapped manifold M 311, where K is the number of optimal atlases. To map each image in the database to manifold M, the system can calculate a d-dimension feature descriptor F 312 such that in M, the Euclidean distance of the feature descriptors from similar atlases is small, while the Euclidean distance of feature descriptors from dissimilar atlases is large.

For an image I, triplet metric learning can pair it with a similar image $I^+$ and a dissimilar image $I^-$ to form a triplet $(I, I^+, I^-)$ 313. The cost function for training can be designed to give similar pairs small values and dissimilar pairs large values. The triplet terms can also be combined with similar pair-wise term for robustness to noise and artifacts 314. The cost function of the pair-wise term is only to minimize the Euclidean distance of similar pairs.

Figure 9:
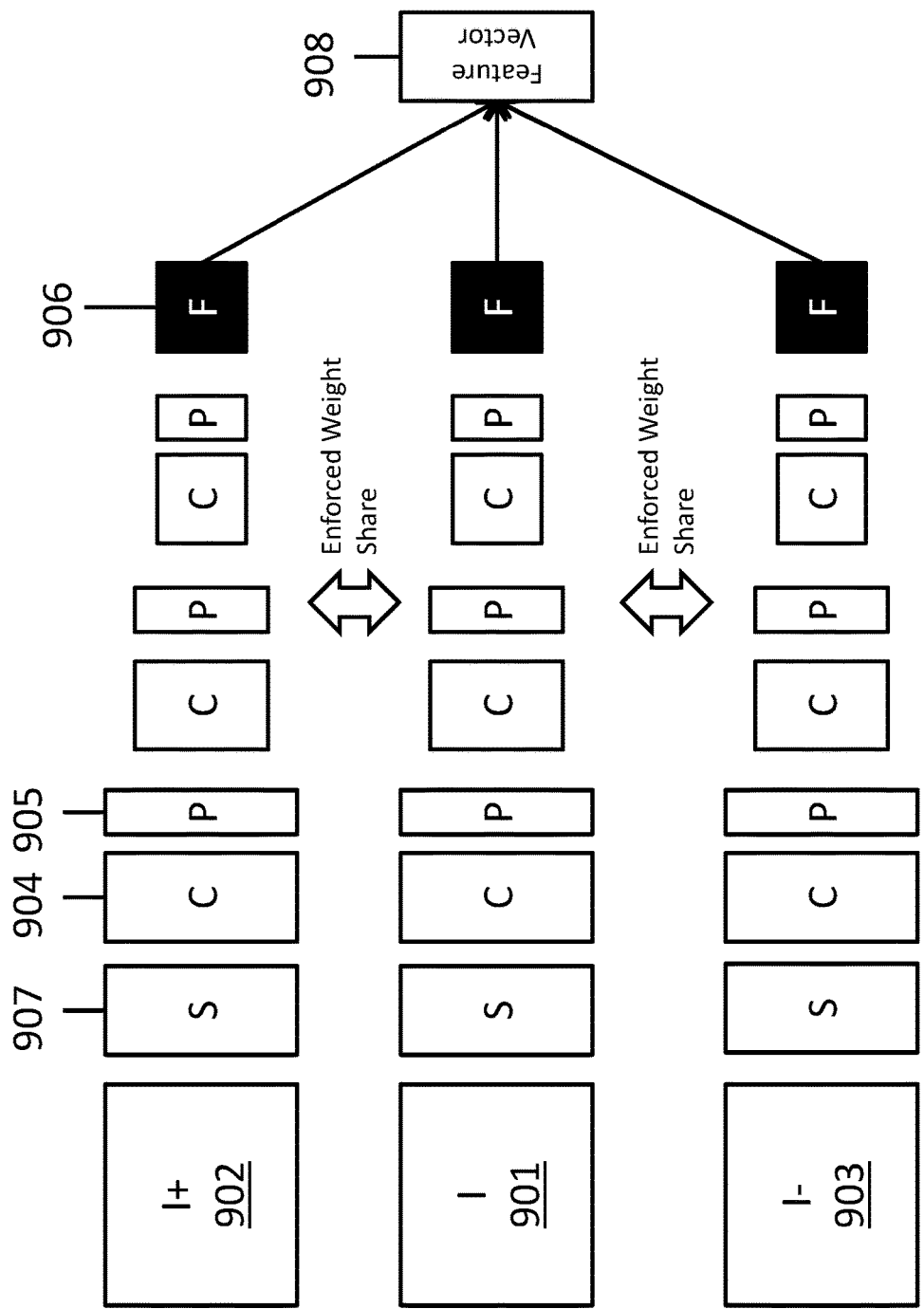
FIG. 9 depicts an illustration of an exemplary network architecture for similarity learning based atlas selection.

An exemplary network architecture for similarity learning based atlas selection is shown in FIG. 9. For each of I 901, $I^+$ 902, and $I^-$ 903, several network layer types, including convergence layers 904, pooling layers 905, fully connective layers 906, and an optional spatial transformer layer 907 can be used to produce a feature vector 908 for the manifold M. The layer types and number of layers in FIG. 9 can be different in alternate embodiments. For instance, non-linearity layers like ReLU can be added to the network. Returning to FIG. 3B, by forming triplets from similar and dissimilar pairs, the system can train a triplet network to learn atlas selection.

In atlas based approaches, atlases can be selected for each organ to accommodate inter-subject variability. To select atlases per organ, the system can use ground truth annotations of the organ to form similar and dissimilar pairs 315 based on the difference of the organ masks (e.g., DICE coefficient). If the difference of two organ masks is small, they are a similar pair and vice versa. Once the triplet network is trained, a new testing image, without organ mask input, can be mapped in the manifold M to a location adjacent to the images with similar organ masks 316. Since most of the gross organ difference can be easily compensated by a global affine transform, the system can introduce a spatial transformer layer in the triplet network to reduce the affine difference for atlas selection 317 (also shown as 907 in FIG. 9).

Using similarity learning, the system can also select atlases with both high quality images and high quality annotation to build a hospital specific database onsite. For instance, metal artifacts from teeth implants are often present in head and neck data sets. If an image with metal artifacts is used as atlas, it is difficult to achieve high quality contour propagation due to the influence of distracting streaks present in the images. To select images without artifacts for atlas database, the system can first train a triplet network to map images to a manifold where images with and without metal artifacts are clustered in different regions 318, then the trained network can map a new image in this manifold 319. If the mapped position of the new image in the manifold is close to the cluster of images without metal artifacts, we can consider it as a high quality image and add it to the database 320, and vice versa.

Figure 3C:
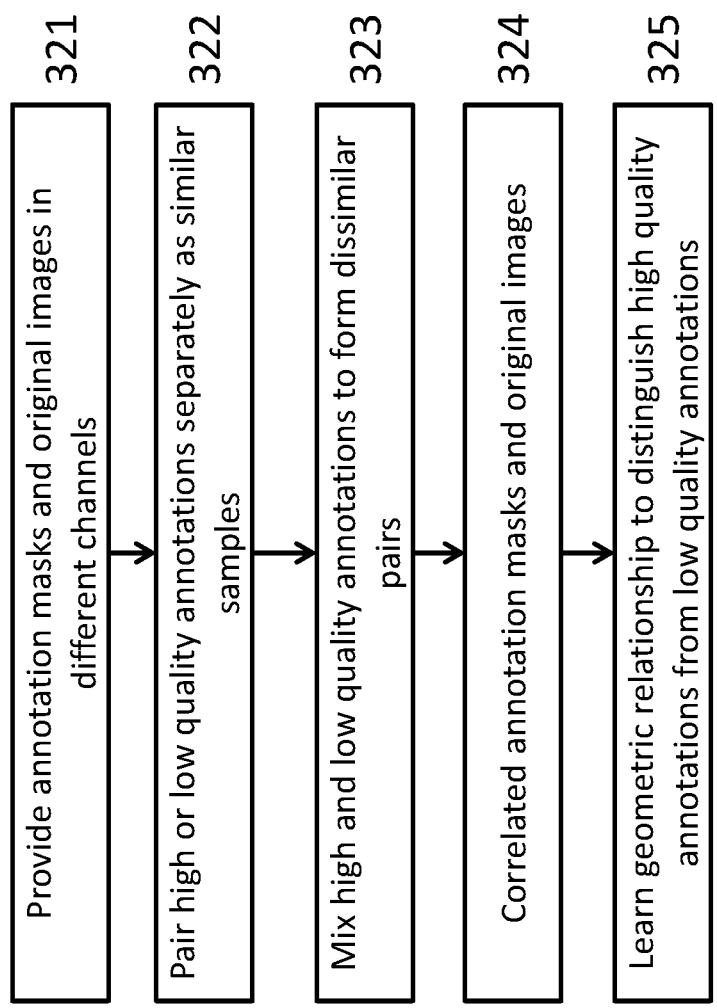
FIG. 3C depicts an illustration describing the selection of a high quality atlas, in accordance with embodiments described herein.

To add an atlas into the database, the system also needs to check its annotation quality. FIG. 3C depicts an illustration describing the selection of a high quality atlas, in accordance with embodiments described herein. Deep similarity learning can also be used to evaluate annotation quality by providing the annotation masks and the original images together into different channels for the triplet network 321. High or low quality annotations can be paired separately as similar samples 322. Then low and high quality annotations can be mixed to form dissimilar pairs 323. During training, the annotation masks and original images can be implicitly correlated 324 and their geometric relationship (contour overlay with the original images) can be learnt to distinguish high low quality annotations from low quality ones 325.

Figure 5:
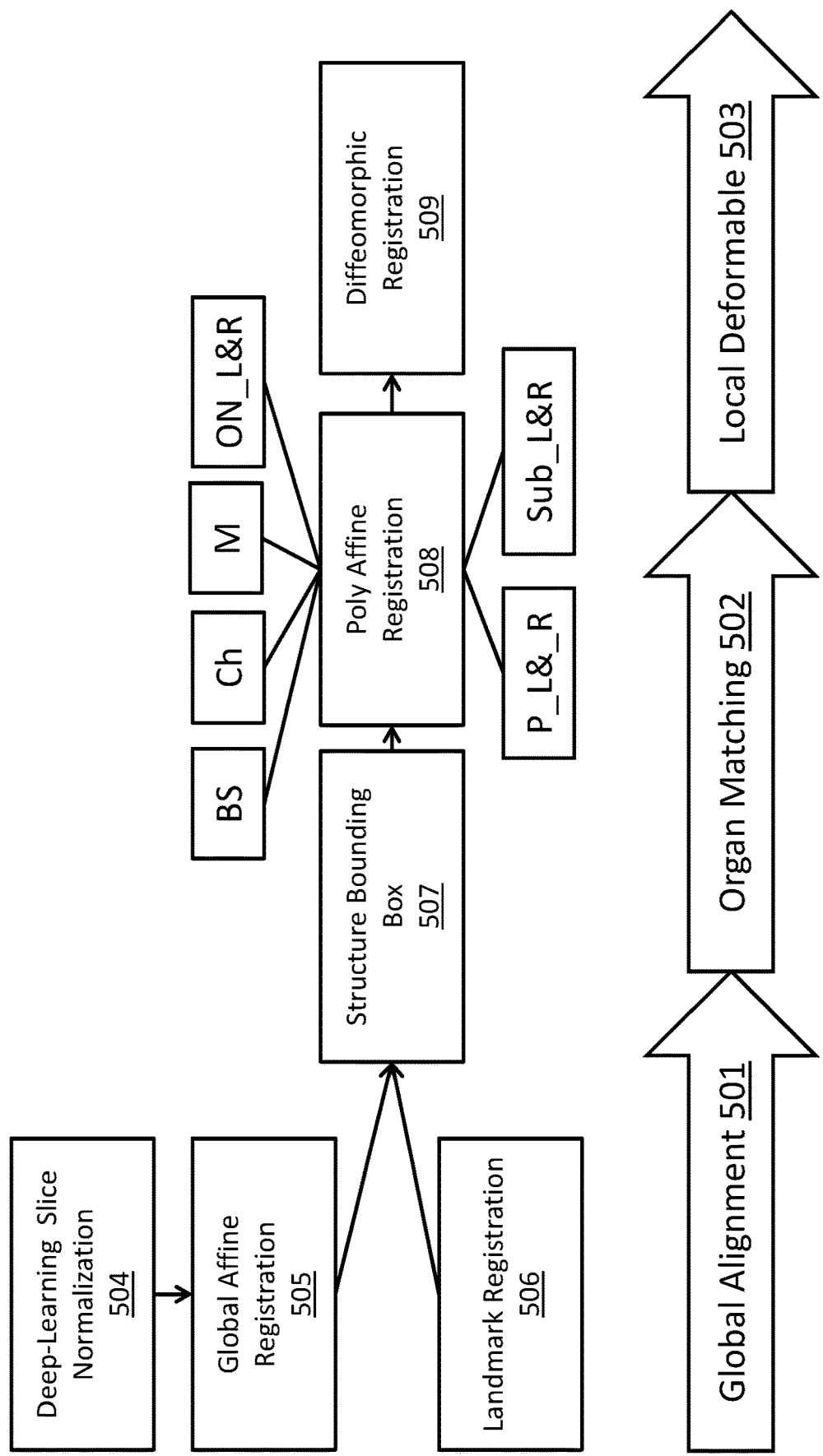
FIG. 5 illustrates global to local image registration from atlas propagation, in accordance with embodiments described herein.

FIG. 5 illustrates global to local image registration from atlas propagation, in accordance with embodiments described herein. Image registration can propagate contours from an atlas to the testing scan, typically using a global to local strategy that proceeds from global alignment 501 to organ matching 502 to a local deformable 503. In an embodiment, atlas and testing image registration can start with a global affine registration 505 to align each organ so that it fits into its region of interest on the target image through a structure bounding box 507, followed by local deformable (or diffeomorphic) registration 509 following a poly affine registration 508.

Because of the variability in the atlas database, an initialization that roughly aligns the atlas and testing scan can be critical for robust contour propagation. In an embodiment, the system can use the same deep learning based slice normalization 504, as was used in constructing the relevant atlas database, for initial alignment along a head-to-feet direction, which can be the direction with largest variability for typical CT or MR scans in radiation therapy. Atlas contour propagation is defined by the deformation field from atlas to the testing. A deep trajectory learning based deformable registration 504 can be used for contour propagation. In an embodiment, the initialization can also be provided by relevant landmark detection and registration 506. The landmarks can be located on or adjacent to the organs at risk. The landmark positons can be detected automatically using machine learning (or deep learning) techniques. The system can also learn the deformation fields with Siamese network of two inputs (atlas and testing image), in combination with an encoder and decoder network. An exemplary implementation is depicted in FIG. 10.

Figure 10:
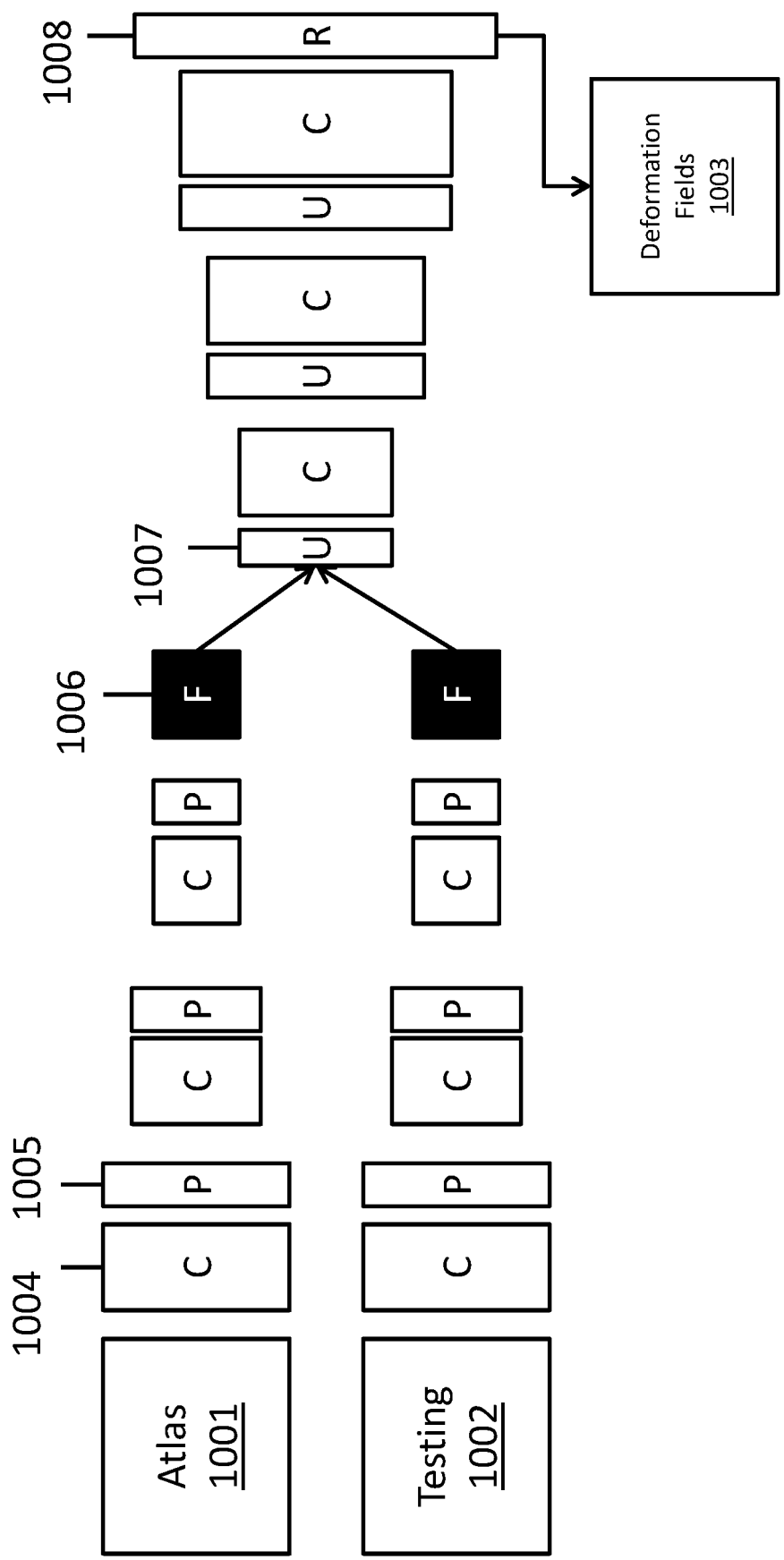
FIG. 10 depicts an illustration of a network used for deformable registration learning, in accordance with embodiments described herein.

FIG. 10 depicts an illustration of a network used for deformable registration learning, in accordance with embodiments described herein. Atlas contour propagation is defined by the deformation field from atlas to the testing. For each of an atlas image 1001 and a testing image 1002, several network layer types, including convergence layers 1004, pooling layers 1005, fully connective layers 1006, unsampling layers 1007, and regression layers 1008 can be used to produce deformation fields 1003 for deformable registration learning. A deep trajectory learning based deformable registration can be used for contour propagation. The system can also learn the deformation fields 1003 with Siamese network of two inputs (atlas 1001 and testing image 1002), in combination with an encoder and decoder network. The layer types and number of layers in FIG. 10 can be different in alternate embodiments.

Figure 6:
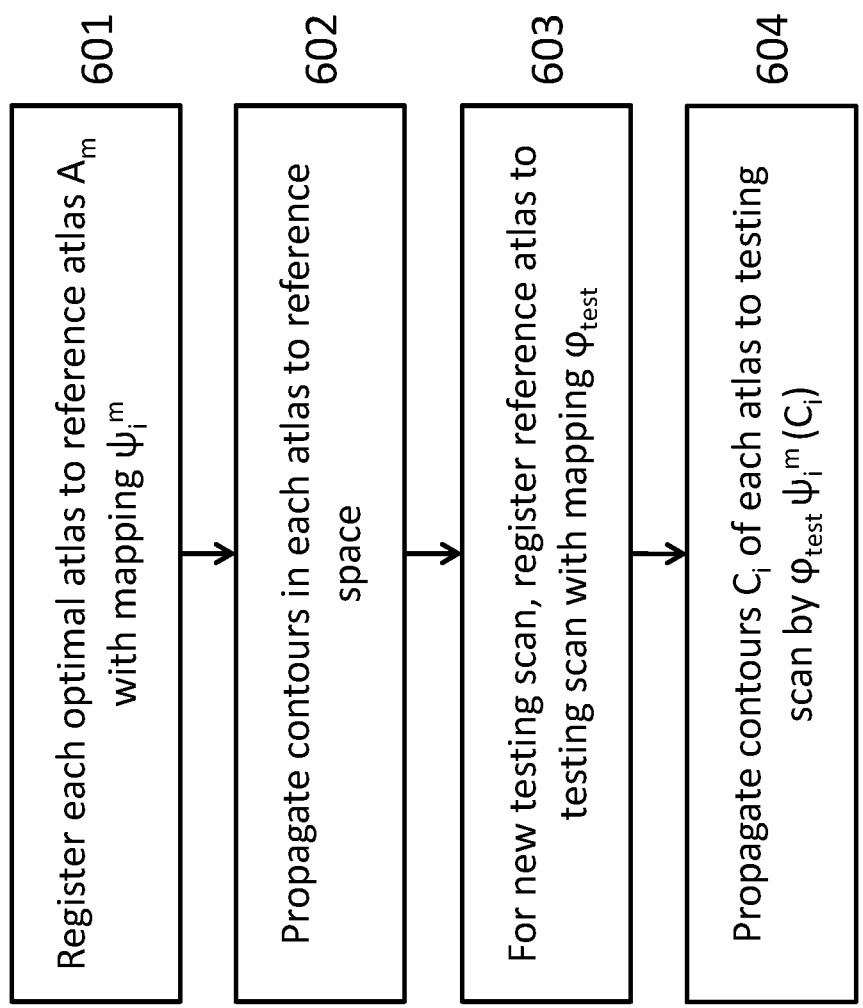
FIG. 6 illustrates mapping compositions through a reference atlas for computation efficiency in atlas propagation, in accordance with embodiments described herein.

FIG. 6 illustrates mapping compositions through a reference atlas for computation efficiency in atlas propagation, in accordance with embodiments described herein. Applying contour propagation described in FIG. 5 to register each atlas to the testing data can result in long computation times, especially if different atlases are used for different organs due to multiple registrations (e.g., a number of the optimal atlases times and a number of OAR). For computational efficiency, in an alternate embodiment, each optimal atlas can be registered to the reference atlas $A_m$ with mapping $\psi_i^m$ 601. Mapping $\psi_i^m$ can also propagate the contours in each atlas to the reference atlas space 302. Then for a new testing scan, the system can register the reference atlas to the testing scan with mapping $\phi_{test}$ 603. Finally, the contours $C_i$ of each atlas can be propagated to the testing scan by $\phi_{test} \psi_i^m (C_i)$ 604. In this way, the total number of inline registrations can be reduced to two (registration $\psi_{test}$ for optimal atlas selection and registration $\phi_{test}$ for contour propagation). If inverse consistency is embedded in the registration, the system can use one registration to get both $\psi_{rest}$ and $\phi_{test}$.

Figure 7A:
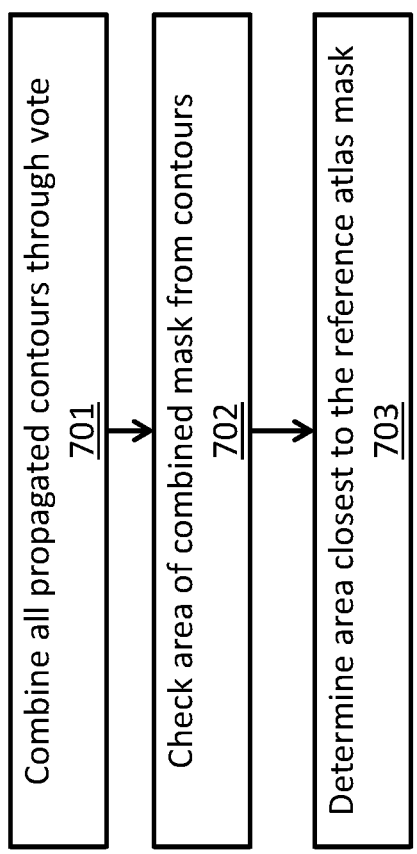
FIGS. 7A-7D depict illustrations further describing methods of atlas fusion, in accordance with embodiments described herein.
Figure 7B:
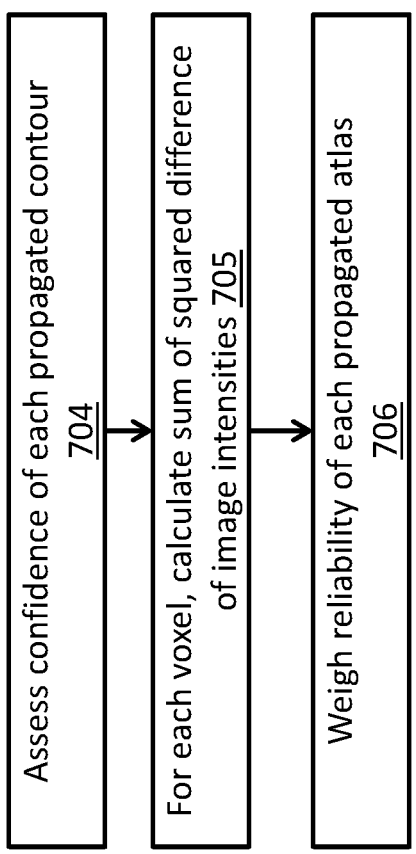
Figure 7C:
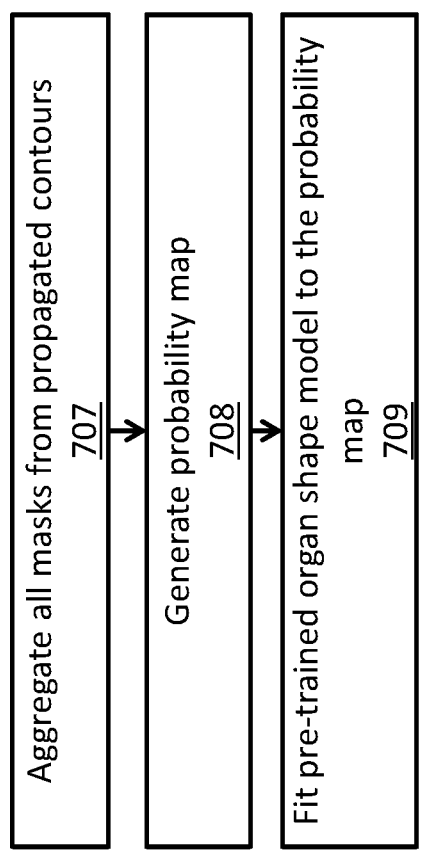

FIGS. 7A-7C depict illustrations further describing methods of atlas fusion, in accordance with embodiments described herein. In an embodiment, atlas fusion can combine all the propagated contours through voting 701, and can provide a final contouring for the testing scan. In an embodiment, majority vote can be used for the combination. In an embodiment, the system can improve the majority vote by checking the area of the combined mask from contours 702 and determining the mask closest to the mask of the reference atlas 703. This process can be termed adaptive voting.

In an alternate embodiment, atlas fusion can be improved using patch-based weighting. First, the confidence of each propagated contour can be assessed 704 on a voxel basis by patch-based context similarity between the target image and the propagated atlas image. For each voxel, the sum of squared difference (or normalized cross correlation) of image intensities can be calculated 705 between the patches (one from the target, and the other from the atlas image) centered at the voxel. These metrics can be used to weight the reliability of each propagated atlas when performing atlas fusion 706, and thus refine the segmentation results on voxel level. This patch-based fusion approach can substantially reduce the impact of local registration errors from propagated atlases.

In an alternate embodiment, atlas fusion can be improved using a probability shape model. First, the system can aggregate all the masks from the propagated contours 707, at which point the system can generate a probability map 708. A pre-trained organ shape model can then be fit to the probability map 709 for contour regularization and smoothing, and thus improve the segmentation accuracy and robustness.

Figure 7D:
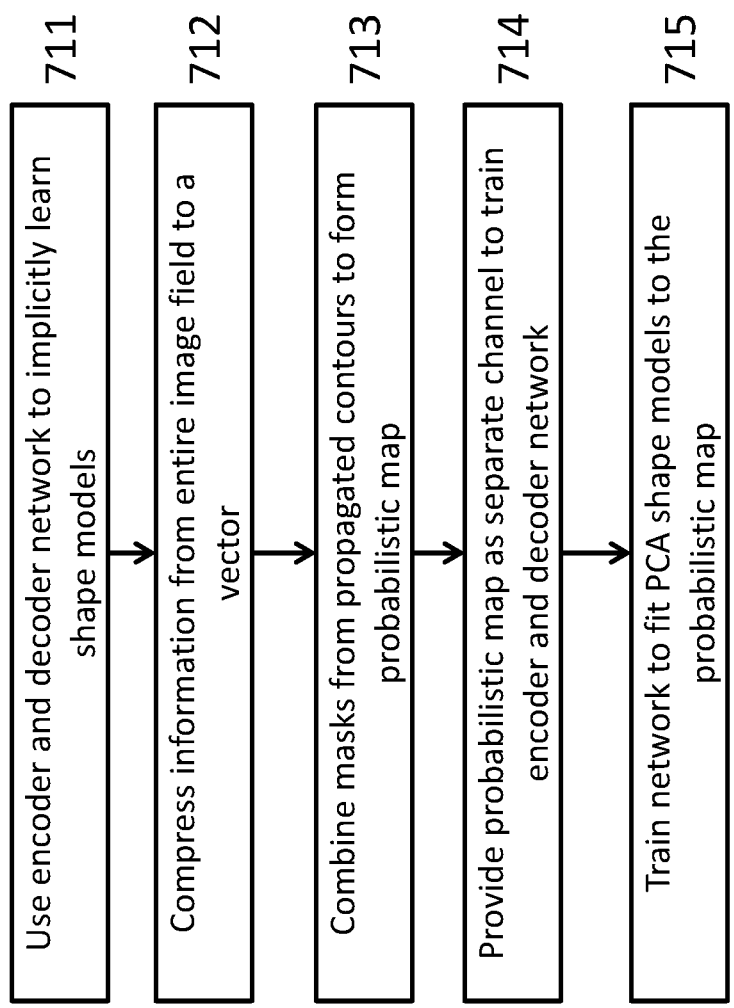

FIG. 7D depicts an illustration of a method of atlas fusing using an encoding and decoding probabilistic map. Traditional atlas fusion aggregates the propagated masks (from contours) by local information without shape priors or models, consequently the final results are likely non-smooth or unrealistic with isolated contours. The system can use an encoder and decoder network to implicitly learn the shape models 711. At the end of the encoder network, the information from the entire image field can be compressed to a vector with a limited number of parameters 712. This encoding step is analogous to, for example, using PCA for shape modeling. The difference of encoding from traditional PCA modeling is that instead of explicitly using PCA to model various shapes, the system can have embed shape models in the network with much higher flexibility to truly represent natural anatomic shapes.

The masks from propagated contours can be combined to form a probabilistic map 713, and then together with the original testing image, this probabilistic map can be provided as a separate channel to train the encoder and decoder network 714. Using the combination of original images and probabilistic maps, the network can take into account both original image information and propagated atlas information (probabilistic map) for fusion, as well being trained to fit PCA shape model encoding to the probabilistic map 715.

Figure 11:
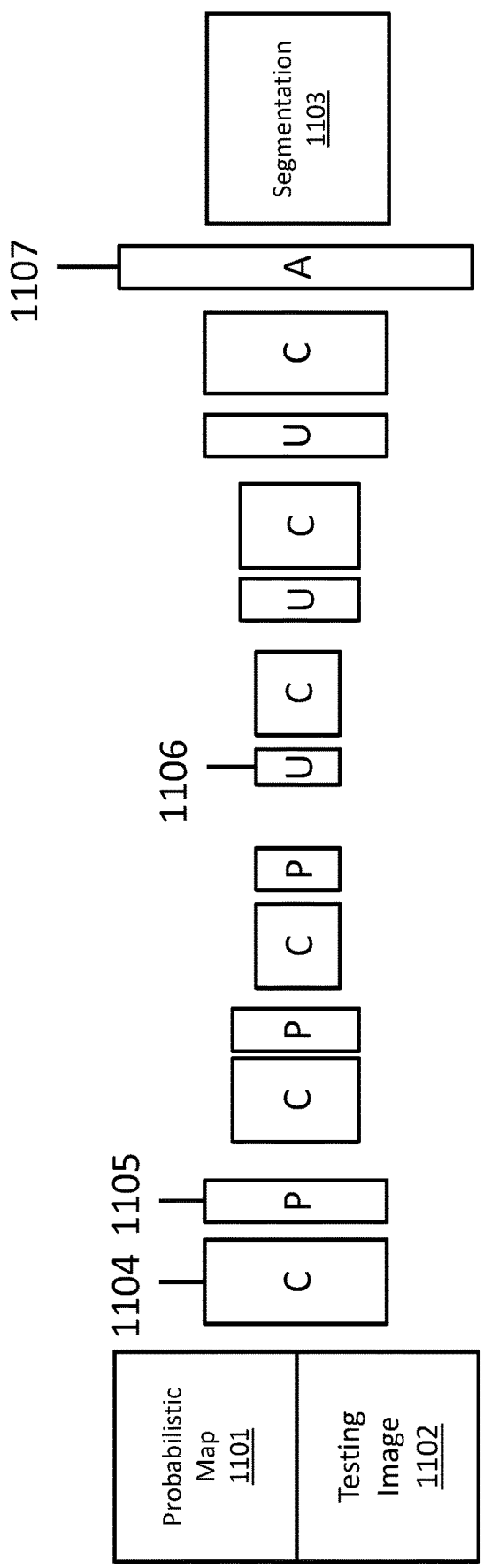
FIG. 11 depicts an illustration of a network architecture for atlas fusion, in accordance with embodiments described herein.

FIG. 11 depicts an illustration of a network architecture for atlas fusion, in accordance with embodiments described herein. For each of the probabilistic map 1101 and testing images 1102, several network layer types, including convergence layers 1104, pooling layers 1105, unsampling layers 1006, and activation layers 1007 can be used to produce a segmentation 1103 for deformable registration learning. The layer types and number of layers in FIG. 11 can be different in alternate embodiments.

Figure 12:
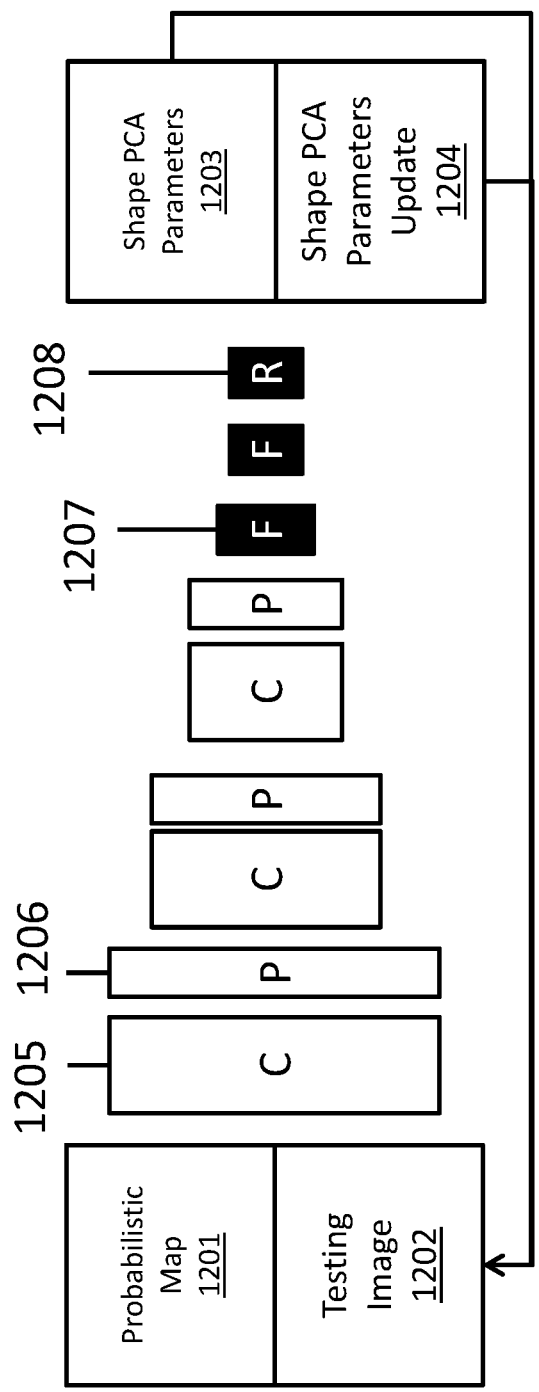
FIG. 12 depicts an illustration of an alternate network architecture for atlas fusion, in accordance with embodiments described herein.

FIG. 12 depicts an illustration of an alternate network architecture for atlas fusion, in accordance with embodiments described herein. The system can also train a network to fit PCA shape models to probabilistic maps by learning the PCA parameters 1203 or PCA parameter updates 1204. A spatial transformer layer can also be used here. For each of the probabilistic map 1201 and testing images 1202, several network layer types, including convergence layers 1205, pooling layers 1206, fully connective layers 1207, and regression layers 1208 can be used. The layer types and number of layers in FIG. 12 can be different in alternate embodiments.

The atlas selection, propagation, and fusion networks can be either trained separately as an individual network, or jointly as an end-to-end system. In practice, it may be more common to train the atlas selection network separately for pre-processing to build the atlas database (offline), then train atlas propagation and fusion together for inline processing. The atlas selection network can also be combined with other learning based segmentation approaches (e.g., SegNet) to select high quality training samples for robust and accurate performance.

Figure 8:
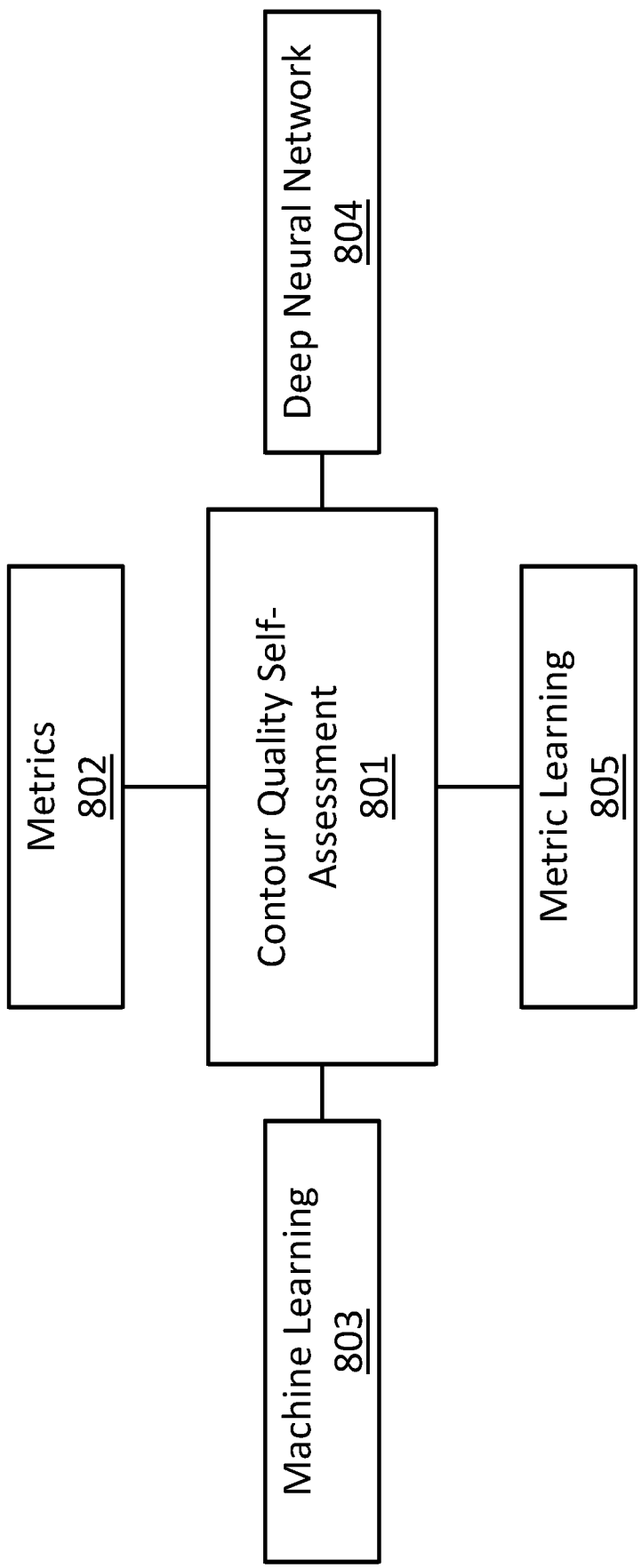
FIG. 8 illustrates methods of contour quality assessment, in accordance with embodiments described herein.

FIG. 8 illustrates methods of contour quality self-assessment, in accordance with embodiments described herein. In many clinical applications, it is highly demanded for an automated system to have the capability of self-assessment, that is, to evaluate the quality of its own outputs and determine if such results shall be presented to a user or display a warning message instead. In order to self-assess the quality of contour 801, the system can use geometry or shape metrics 802, for instance, roundness, compactness, and/or smoothness etc. Alternately, the system can use a machine learning approach 803, such as support vector machine, probabilistic trees, or random forests, to learn how to assess the quality. This machine learning approach can be either classification ("good" vs. "bad") or regression to predict the quality of contours in a continuous range. Alternately, such a machine learning approach 803 can also be a deep neural network 804. Alternately, a metric learning 805, borrowed from a documentation retrieval field, can also be used for assess contour quality. The metric learning approach can be either deep neural network based or non-deep learning based. Examples of deep neural network for metric learning can include, but are not limited to, Siamese networks or triplet networks.

The system can be further extended to learn the atlas from annotations and edits to continuously improve with reinforcement learning. In one implementation, testing images and current annotation can be the current state, edit can be the action, the reward can be the closeness to the final ground truth annotation, as well as the options of the number, amount, extent, and location of the editing. The reward can also be any combination of the above mentioned measures. Atlas and organ shape variability can also be encoded with deep neural network via, for example, a generative model.

Figure 13:
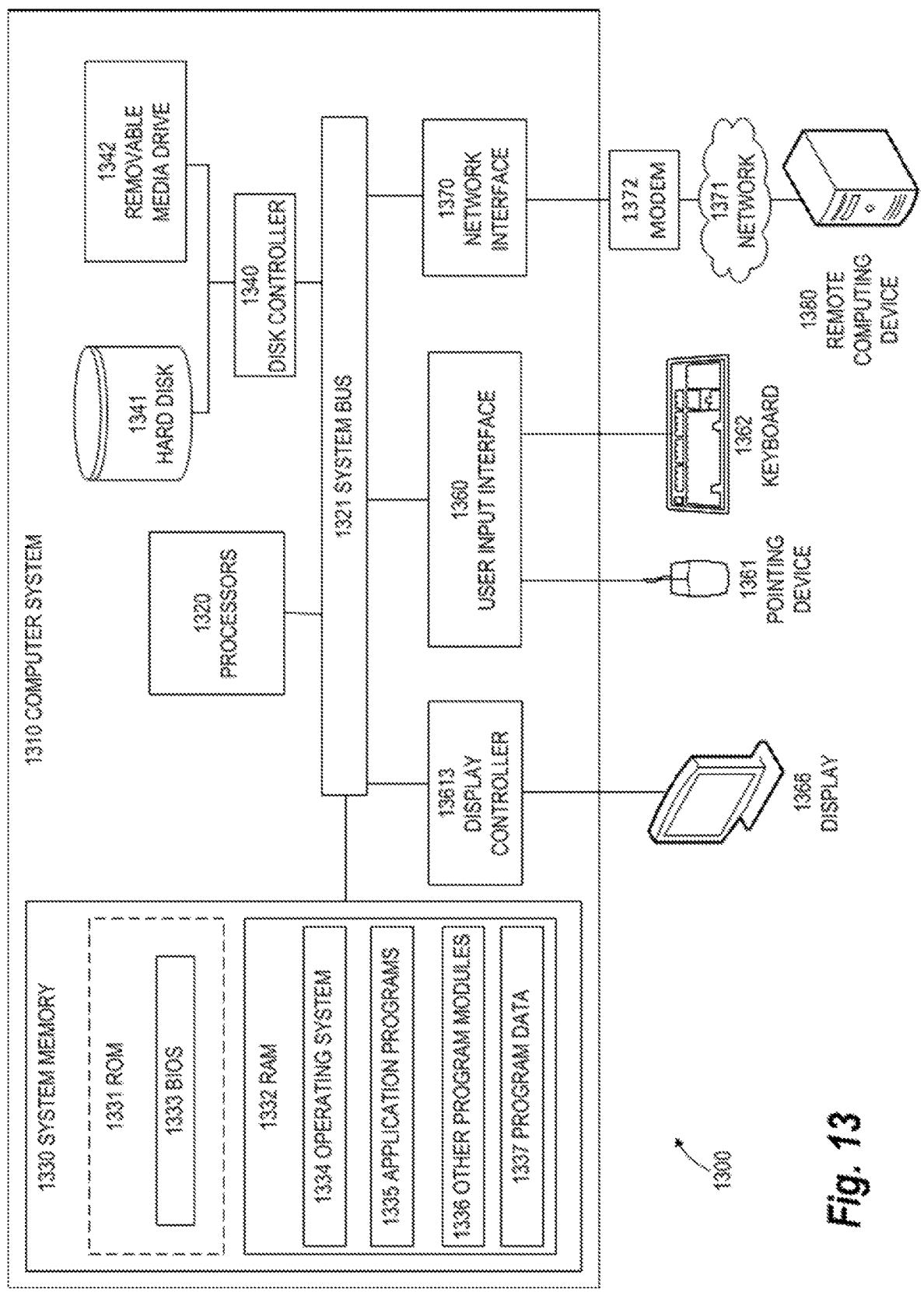
FIG. 13 illustrates an exemplary computing environment within which embodiments of the invention may be implemented.

FIG. 13 illustrates an exemplary computing environment 1300 within which embodiments of the invention may be implemented. For example, the computing environment 1300 may be used to implement one or more of the components illustrated in the system as described. The computing environment 1300 may include computer system 1310, which is one example of a computing system upon which embodiments of the invention may be implemented. Computers and computing environments, such as computer system 1310 and computing environment 1300, are known to those of skill in the art and thus are described briefly here.

As shown in FIG. 13, the computer system 1310 may include a communication mechanism such as a bus 1321 or other communication mechanism for communicating information within the computer system 1310. The computer system 1310 further includes one or more processors 1320 coupled with the bus 1321 for processing the information. The processors 1320 may include one or more central processing units (CPUs), graphical processing units (GPUs), or any other processor known in the art.

The computer system 1310 also includes a system memory 1330 coupled to the bus 1321 for storing information and instructions to be executed by processors 1320. The system memory 1330 may include computer readable storage media in the form of volatile and/or nonvolatile memory, such as read only memory (ROM) 1331 and/or random access memory (RAM) 1332. The system memory RAM 1332 may include other dynamic storage device(s) (e.g., dynamic RAM, static RAM, and synchronous DRAM). The system memory ROM 1331 may include other static storage device(s) (e.g., programmable ROM, erasable PROM, and electrically erasable PROM). In addition, the system memory 1330 may be used for storing temporary variables or other intermediate information during the execution of instructions by the processors 1320. A basic input/output system (BIOS) 1333 containing the basic routines that help to transfer information between elements within computer system 1310, such as during start-up, may be stored in ROM 1331. RAM 1332 may contain data and/or program modules that are immediately accessible to and/or presently being operated on by the processors 1320. System memory 1330 may additionally include, for example, operating system 1334, application programs 1335, other program modules 1336 and program data 1337.

The computer system 1310 also includes a disk controller 1340 coupled to the bus 1321 to control one or more storage devices for storing information and instructions, such as a hard disk 1341 and a removable media drive 1342 (e.g., floppy disk drive, compact disc drive, tape drive, and/or solid state drive). The storage devices may be added to the computer system 1310 using an appropriate device interface (e.g., a small computer system interface (SCSI), integrated device electronics (IDE), Universal Serial Bus (USB), or FireWire).

The computer system 1310 may also include a display controller 13613 coupled to the bus 1321 to control a display 1366, such as a cathode ray tube (CRT) or liquid crystal display (LCD), for displaying information to a computer user. The computer system includes an input interface 1360 and one or more input devices, such as a keyboard 1362 and a pointing device 1361, for interacting with a computer user and providing information to the processor 1320. The pointing device 1361, for example, may be a mouse, a trackball, or a pointing stick for communicating direction information and command selections to the processor 1320 and for controlling cursor movement on the display 1366. The display 1366 may provide a touch screen interface which allows input to supplement or replace the communication of direction information and command selections by the pointing device 1361.

The computer system 1310 may perform a portion or all of the processing steps of embodiments of the invention in response to the processors 1320 executing one or more sequences of one or more instructions contained in a memory, such as the system memory 1330. Such instructions may be read into the system memory 1330 from another computer readable medium, such as a hard disk 1341 or a removable media drive 1342. The hard disk 1341 may contain one or more data stores and data files used by embodiments of the present invention. Data store contents and data files may be encrypted to improve security. The processors 1320 may also be employed in a multi-processing arrangement to execute the one or more sequences of instructions contained in system memory 1330. In alternative embodiments, hard-wired circuitry may be used in place of or in combination with software instructions. Thus, embodiments are not limited to any specific combination of hardware circuitry and software.

As stated above, the computer system 1310 may include at least one computer readable medium or memory for holding instructions programmed according to embodiments of the invention and for containing data structures, tables, records, or other data described herein. The term "computer readable medium" as used herein refers to any medium that participates in providing instructions to the processor 1320 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 1341 or removable media drive 1342. Non-limiting examples of volatile media include dynamic memory, such as system memory 1330. Non-limiting examples of transmission media include coaxial cables, copper wire, and fiber optics, including the wires that make up the bus 1321. Transmission media may also take the form of acoustic or light waves, such as those generated during radio wave and infrared data communications.

The computing environment 1300 may further include the computer system 1310 operating in a networked environment using logical connections to one or more remote computers, such as remote computer 1380. Remote computer 1380 may be a personal computer (laptop or desktop), a mobile device, a server, a router, a network PC, a peer device or other common network node, and typically includes many or all of the elements described above relative to computer system 1310. When used in a networking environment, computer system 1310 may include modem 1372 for establishing communications over a network 1371, such as the Internet. Modem 1372 may be connected to bus 1321 via user network interface 1370, or via another appropriate mechanism.

Network 1371 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 1310 and other computers (e.g., remote computer 1380). The network 1371 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 1371.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A computer-implemented method for atlas-based contouring of images, the method comprising:
   receiving a testing scan;
   constructing a relevant atlas database comprising scans or scan partitions that have a similar body region to the testing scan;
   acquiring a reference atlas from the relevant atlas database;
   for each atlas in the relevant atlas database, determining a mapping to the reference atlas;
   determining a test mapping of the test scan to the reference atlas;
   selecting one or more optimal atlases from the relevant atlas database based on a comparison of the test mapping of the test data set and the mappings of each atlas in the relevant atlas database;
   propagating the optimal atlases to the testing scan to yield one or more propagated contours;
   if the propagated contours comprise more than one propagated contour, fusing the propagated contours into a final contour; and
   assessing the quality of the one or more propagated contours using a machine learning model trained to classify each propagated contour according to a plurality of geometry or shape metrics.

2. The method as recited in claim 1, wherein the relevant atlas database is constructed using a process comprising:
manually annotating one or more anatomical landmarks on a subset of full body volumes;
estimating an average position for each of the one or more anatomical landmarks;
annotating the one or more anatomical landmarks on a remainder of full body volumes;
labelling one or more slices by linear interpolation;
regressing one or more slice locations in a normalized range; and
using the labeled slice to populate the relevant atlas database with the one or more scans having the similar body region to the testing scan.

3. The method as recited in claim 2, wherein the one or more anatomical landmarks comprise one or more of: a head top, a neck, a lung top, a spine, a knee, and a foot.

4. The method as recited in claim 1, further comprising:
defining, by a user, one or more organ templates for one or more testing data sets from a mixed body region database;
extending the one or more organ templates as comprehensive representations of required contouring.

5. The method as recited in claim 4, further comprising:
extending the one or more organ templates as a comprehensive representation of one or more of: image modality and quality, organ shape and appearance, and annotation protocol.

6. The method as recited in claim 1, further comprising:
selecting the reference atlas using a medium of a sum of one or more squared values of the mapping determined for each atlas in the relevant atlas database.

7. The method as recited in claim 1, wherein the mapping of each atlas to the reference atlas is either (i) affine or (ii) affine and deformable.

8. The method as recited in claim 1, further comprising:
performing a deep learning based slice normalization for each atlas in the relevant atlas database; and
performing a global affine registration to align one or more organs for each atlas in the relevant atlas database such that the one or more organs fit into a region of interest on the target scan.

9. The method as recited in claim 1, further comprising:
registering each of the one or more optimal atlases to a reference atlas $A_m$ with a mapping $\psi_i^m$;
for each optimal atlas, propagating one or more contours to a reference space;
registering the reference atlas to a testing scan using a mapping $\phi_{test}$; and
for each atlas, propagating one or more contours $C_i$ of each atlas to the testing scan by $\phi_{test} \psi_i^m (C_i)$.

10. The method as recited in claim 1, wherein the propagated contours are fused into the final contour by combining the one or more propagated contours through vote collection.

11. The method as recited in claim 1, further comprising:
assessing a confidence of each of the one or more propagated contours;
for each of one or more voxels, calculating a sum of a squared difference of image intensities; and
weighing a reliability of each of the one or more propagated contours.

12. The method as recited in claim 1, further comprising:
aggregating a mask from each of the one or more propagated contours;
generating a probability map; and
fitting a pre-trained organ shape model to the probability map.

13. The method as recited in claim 12, further comprising:
using an encoder and decoder network to implicitly learn shape models;
compressing information from an entire image field to a vector;
combining the masks to form the probabilistic map;
providing the probabilistic map as a separate channel to train the encoder and decoder network; and
training the encoder and decoder network to fit one or more PCA shape models to the probabilistic map.

14. The method as recited in claim 1, wherein the assessing the quality of one or more propagated contours is performed using at least one of metrics, machine learning, a deep neural network, and metric learning.

15. A computer program product for atlas-based contouring, the computer program product comprising a non-transitory computer readable storage medium having program instructions embodied therewith, the program instructions executable by a processor to cause the processor to:
construct a relevant atlas database by selecting one or more scans or scan partitions from a mixed body region database;
acquire a reference atlas from the relevant atlas database;
for each atlas in the relevant atlas database, determine a mapping to the reference atlas;
determine a test mapping of the test scan to the reference atlas;
select one or more optimal atlases from the relevant atlas database based on a comparison of the test mapping of the test data set and the mappings of each atlas in the relevant atlas database;
propagate the optimal atlases to the testing scan to yield one or more propagated contours;
if the propagated contours comprise more than one propagated contour, fuse the propagated contours into a final contour; and
assess the quality of the one or more propagated contours using a machine learning model trained to classify each propagated contour according to a plurality of geometry or shape metrics.

16. A system for atlas-based contouring, comprising a processor configured to:
construct a relevant atlas database by selecting one or more scans or scan partitions from a mixed body region database;
acquire a reference atlas from the relevant atlas database;
for each atlas in the relevant atlas database, determine a mapping to the reference atlas;
determine a test mapping of the test scan to the reference atlas;
select one or more optimal atlases from the relevant atlas database based on a comparison of the test mapping of the test data set and the mappings of each atlas in the relevant atlas database;
propagate the optimal atlases to the testing scan to yield one or more propagated contours;
if the propagated contours comprise more than one propagated contour, fuse the propagated contours into a final contour; and
assess the quality of the one or more propagated contours using a machine learning model trained to classify each propagated contour according to a plurality of geometry or shape metrics.

* * * * *